United States Patent [19]

Sabahi et al.

[11] Patent Number: 5,399,279
[45] Date of Patent: Mar. 21, 1995

[54] REFRIGERATION COMPOSITIONS

[75] Inventors: Mahmood Sabahi, Baton Rouge, La.; Matthew L. Hurst, Lafayette, Ind.

[73] Assignee: Albemarle Corporation, Richmond, Va.

[21] Appl. No.: 986,204

[22] Filed: Dec. 7, 1992

Related U.S. Application Data

[63] Continuation-in-part of Ser. No. 947,628, Sep. 21, 1992, abandoned, which is a continuation-in-part of Ser. No. 812,398, Dec. 23, 1991, abandoned.

[51] Int. Cl.$^6$ .................. C09K 5/04; C10M 105/42
[52] U.S. Cl. .................... 252/68; 252/56 R; 252/56 S; 252/67
[58] Field of Search ............ 252/50, 56 R, 56 S, 252/68, 67

[56] References Cited

U.S. PATENT DOCUMENTS

| | | | |
|---|---|---|---|
| 2,396,626 | 3/1946 | Wiest et al. | 558/368 |
| 4,944,890 | 8/1990 | Deeb et al. | 252/54 |
| 5,021,179 | 6/1991 | Zehler et al. | 252/68 |
| 5,096,606 | 3/1992 | Hagihara et al. | 252/68 |

FOREIGN PATENT DOCUMENTS 0430657 6/1991 European Pat. Off. .
90/12849 11/1990 WIPO .

Primary Examiner—Christine Skane
Attorney, Agent, or Firm—Richard J. Hammond; Patricia J. Hogan

[57] ABSTRACT

Ester oils that (1) correspond to the formula ROOC-$CH_2CH_2$-(ROOC-$CHCH_2$)$_m$-C(COOR)$_2$-($CH_2CHCOOR$)$_n$-$CH_2CH_2COOR$ in which the R's represent alkyl groups of 1–30 carbons and the sum of m and n in the molecules is an average of 0–30 and (2) have viscosities suitable for refrigeration lubricants can be given excellent miscibility with fluorohydrocarbon refrigerants, such as R-134a, when at least 10% of the R groups contain 1–4 carbons.

16 Claims, No Drawings

REFRIGERATION COMPOSITIONS

CROSS-REFERENCE TO RELATED APPLICATION

This application is a continuation-in-part of application Ser. No. 07/947,628, filed Sep. 21, 1992, now abandoned which in turn is a continuation-in-part of application Ser. No. 07/812,398, filed Dec. 23, 1991, now abandoned.

FIELD OF INVENTION

The invention relates to refrigeration compositions and more particularly to such compositions containing novel ester lubricants.

BACKGROUND

Many natural and synthetic materials are known to be useful as lubricants, their utility in particular applications depending on factors such as their stability and viscosity under the conditions of use, their pour points, and their compatibility with any materials with which they will be used.

In refrigeration applications (e.g., home-use or industrial-use refrigerators, freezers, or air conditioners for buildings, automobiles, airplanes, and other vehicles), the need to replace chlorofluorocarbon refrigerants with a refrigerant having lesser ozone-depleting potential has made it important to find lubricants which would be suitable for use with 1,1,1,2-tetrafluoroethane (R-134a), a refrigerant that has been reported to have an ozone depletion potential of zero. Mineral oils, usually the refrigeration lubricants of choice in the past, cannot be utilized in this application because of incompatibility with R-134a.

As shown, e.g., in Jolley, "New and Unique Lubricants for Use in Compressors Utilizing R-134a Refrigerant," pp. 145-152 (a paper presented at the ASHRE/Refrigeration/Compressor Engineering Conference at Purdue University, July 1990), oils of various types, including polyalkylene glycols, esters, and amides, have been found to have sufficient compatibility with R-134a to justify further investigation. However, there is still a need for lubricants to be used in this application, as well as in other lubricant applications.

The Michael reaction is a known process wherein a Michael acceptor (such as an α,β-ethylenically-unsaturated ester) is reacted with a Michael donor (such as a dialkyl malonate) to elongate a carbon chain. As indicated in Skarzewski, "The Michael Reaction of Methanetricarboxylic Esters. A Simple Method for Two-Carbon Chain Elongation." *Synthesis*, December 1990, pp. 1125-1127, it has usually been considered undesirable to add a donor molecule to more than one acceptor molecule in such a reaction. However, U.S. Pat. No. 2,396,626 (Wiest et al.) teaches that products useful as plasticizers or solvents can be obtained by reacting two molecules of an alkyl acrylate with a molecule of a donor, such as an ester of malonic acid, phenylacetic acid, cyanoacetic acid, or acetoacetic acid.

Copending application Ser. No. 07/947,628 (Sabahi) discloses ester oils corresponding to the formula ROOC-$CH_2CH_2$-(ROOC-CHCH$_2$)$_m$-C(COOR)$_2$-(CH$_2$CHCOOR)$_n$-CH$_2$CH$_2$-COOR in which the R's represent one or more alkyl groups of 1-30 carbons and the sum of m and n in the molecules is an average of 1-10. These ester oils can be prepared by a Michael reaction so as to have viscosities of 1-600 $mm^2.s^{-1}$ and have been discovered to be useful as refrigeration lubricants. Some of them, however, have insufficient compatibility with R-134a to be employed therewith.

SUMMARY OF INVENTION

It has been found that the aforementioned ester oils of Sabahi can be provided with both excellent R-134a compatibility and a viscosity suitable for a refrigeration lubricant when they contain a sufficient number of lower alkyl groups in the molecules. Thus, the invention resides in compositions comprising a fluorohydrocarbon refrigerant and, as a refrigeration lubricant, at least one oil corresponding to the formula ROOC-$CH_2CH_2$-(ROOC-CHCH$_2$)$_m$-C(COOR)$_2$-(CH$_2$CHCOOR)$_n$-CH$_2$CH$_2$COOR in which the R's represent alkyl groups of 1-30 carbons, at least 10% of which are alkyl groups of 1-4 carbons; each of m and n is zero or a positive integer; and the sum of m and n in the molecules is an average of 0-30.

DETAILED DESCRIPTION

The fluorohydrocarbon refrigerants with which the novel lubricants are employed may be refrigerants consisting of one or more fluorohydrocarbons, such as difluoromethane (R-32), 1,1,2,2,2-pentafluoroethane (R-125), 1,1,2,2-tetrafluoroethane (R-134), 1,1,1,2-tetrafluoroethane (R-134a), 1,1,1-trifluoroethane (R-143a), 1,1-difluoroethane (R-152a). Alternatively, they may be mixtures of one or more fluorohydrocarbons with one or more other refrigerants, e.g., hydrocarbons such as methane, ethane, propane (R-290), butane, ethylene, and propylene; and halocarbons and/or halohydrocarbons such as chlorotrifluoromethane, dichlorodifluoromethane, dichlorofluoromethane, chlorodifluoromethane (R-22), 1,2,2-trifluoro-1,1,2-trichloroethane, 1,1-dichloro-2,2,2-trifluoroethane (R-123), 1,1-dichloro-1-fluoroethane, 1-chloro-2,2,2-trifluoroethane, 1-chloro-1,2,2,2-tetrafluoroethane (R-124), 1-chloro-1,1,2,2-tetrafluoroethane, and dichloromethane. Among the refrigerant blends with which the lubricants can be advantageously used are the binary mixtures of R-32 with R-125, R-152a, or R-134a; R-125/R-143a, R-290/R-134a, and R-22/R-152a binary blends; and ternary blends such as R-22/R-290/R-125, R-22/R-152a/R-124, R-32/R-125/R-134a, and R-125/R-143a/R-134a.

The lubricants of the invention have a structure such as to make it most convenient to prepare them via a Michael-type reaction. When produced directly by a Michael reaction, they are synthesized by reacting one or more dialkyl malonates with one or more alkyl acrylates selected so that the product contains at least the required number of lower alkyl groups. However, the lubricants may also be prepared by forming such a Michael product and then subjected it to a transesterification reaction in which some of the lower alkyl groups are replaced with higher alkyl groups.

Michael donors and Michael acceptors which can be used in the reaction include all dialkyl malonates and alkyl acrylates in which the alkyl groups contain 1-30 carbons, although (1) the donors which are sufficiently reactive to permit a reasonably fast reaction are apt to be preferred and (2) it is, of course, necessary for at least one of the reactants to contain alkyl groups of 1-4 carbons. The alkyl groups in such compounds are preferably true alkyl groups (i.e., saturated aliphatic hydrocarbyl groups), such as methyl, ethyl, propyl, isopropyl, butyl, isobutyl, t-butyl, pentyl, hexyl, heptyl, octyl, decyl, dodecyl, tetradecyl, hexadecyl, octadecyl, eicosyl, docosyl, tetracosyl, and triacontyl groups, more preferably those containing 1-10 carbons, and most preferably methyl and/or ethyl groups. However, they may also be groups which are predominantly alkyl in nature, i.e., contain one or more atoms other than the carbon and hydrogen of the alkyl groups as hetero atoms (e.g., oxygen, sulfur, or phosphorus atoms) which are part of the chain or as substituent groups (e.g., alkoxy, halo, or cyano groups) but contain so few of the other atoms that the predominantly hydrocarbyl nature of the groups is preserved.

To preserve the predominantly hydrocarbyl nature of the group, the number of hetero atoms or non-hydrocarbyl substituents therein should not exceed 0.3 per carbon and is preferably not more than 0.1 per carbon. These predominantly hydrocarbyl groups can be regarded as being virtually the same as the alkyl groups to which they most closely correspond, so the term alkyl, as used herein, should be understood as including the predominantly alkyl groups as well as the alkyl groups normally denoted by those terms. Exemplary of such groups are chlorohexyl, bromodecyl, ethoxyoctyl, and cyanononyl.

As in Sabahi (the teachings of which are incorporated herein by reference), it is generally preferred to prepare the Michael product by reacting the donor and acceptor in the presence of a basic initiator (preferably an alkali or alkaline earth metal hydroxide, alkoxide, amide, or carbonate) and a phase transfer catalyst (preferably an alkylammonium salt such as the tetraalkylammonium chlorides, bromides, fluorides, iodides, sulfates, hydrogen sulfates, carbonates, and phosphates in which the alkyl groups contain 1-20 carbons) at a suitable temperature, usually a temperature of about 0°-150° C., preferably about 20°-120° C., and most preferably about 60°-110° C.

The reaction is effected by combining the reactants, initiator, and catalyst, optionally in the presence of a solvent, and maintaining contact between the reactants at the selected reaction temperature until the desired degree of reaction has been effected. It is usually preferred to make the Michael acceptor the last of the ingredients to be charged to the reaction vessel in order to achieve better control of the reaction temperature and hence improved direction of the reaction to the formation of a desired product.

Since the reaction normally leads to the formation of a mixture of products containing different numbers of acceptor moieties per molecule, it permits the production of some molecules containing more acceptor moieties than the number that would theoretically be provided by the amount of acceptor employed in the reaction mixture. However, it is necessary for the reaction mixture to contain at least the stoichiometric requirement of the acceptor, and preferably a stoichiometric excess, in order for the product to contain a substantial amount of a desired product molecule. Thus, since the oils having optimum viscosities are usually those in which the molecules contain 1-30 acceptor moieties/donor moiety, it is generally preferred for the acceptor/donor mol ratio in the reaction mixture to be about 1-35/1—the particular ratio used in any given instance varying with the particular type of product desired, e.g., a ratio of about 1-15/1 being used when it is wished to form a product containing about 1-10 acceptor moieties/donor moiety. Particularly preferred lubricants of the invention are ester oils which are prepared so as to have at least three acceptor molecules in at least about 25% of the molecules obtained by the Michael reaction.

The products of the Michael reaction may be liquids or solids, depending on the particular reactants and reactant ratios used; and, as already indicated, they are typically mixtures of compounds containing different numbers of acceptor moieties per molecule. If desired, the individual compounds of the mixture or groups of those compounds (e.g., the relatively low and relatively high molecular weight fractions) may be separated from one another prior to being used in their end application or prior to being subjected to transesterification preparatory to such use. However, such separations are frequently unnecessary and, in fact, sometimes undesirable. Having a product characterized by a wide molecular weight distribution can be an advantage in providing a balance of properties, as is the case with oils which are to be used in refrigeration compositions wherein some relatively high molecular weight portion is desired to give a required viscosity, but some relatively low molecular weight portion is desired to increase compatibility with the refrigerant with which the oil is to be used.

Achieving either a better balance of properties or properties which differ in some other respect from those of the Michael reaction product can also be accomplished by subjecting the product mixture or one or more of the components thereof to transesterification. Such a post-treatment of the Michael product is particularly beneficial in providing products containing ester groups which—if present in one or more of the Michael reactants—would make the reaction relatively slow. Thus, it is apt to be preferred, for example, to react dimethyl malonate with methyl acrylate to provide a first product and then transesterify that product with hexanol to provide an oily second product in which about a third of the functional groups are hexyl ester groups than to prepare an oily Michael reaction product from the slower-reacting dihexyl malonate and methyl acrylate.

Regardless of whether the transesterification is conducted on a recovered or unrecovered intermediate, it is accomplished by contacting the intermediate with one or more alcohols containing more carbons per molecule than the alkyl groups to be replaced and maintaining contact between the reactants at a suitable temperature until the desired transesterification has been effected. Alcohols most apt to be desirable for use in the reaction are substituted and unsubstituted alkanols containing up to about 30 carbons (e.g., ethanol, chloroethanol, propanol, butanol, hexanol, bromohexanol, heptanol, octanol, decanol, fluorodecanol, dodecanol, hexadecanol, octadecanol, eicosanol, tetracosanol, triacontanol, and mixtures thereof), as well as the aliphatic alcohols containing up to 30 carbons and also containing hetero atoms, such as oxygen, phosphorus, or sulfur (e.g., ethylthioethanol, ethoxyethanol, and the like).

The amount of alcohol employed in the transesterification reaction varies with the degree of transesterification desired, the quantity generally being the stoichiometric amount or an amount slightly in excess of the stoichiometric requirement. For example, when the intermediate contains an average of four ester groups per molecule, and it is wished to replace substantially 75% of those ester groups with the alcohol or alcohols used in the transesterification reaction, the amount of alcohol added to the intermediate should be three mols or slightly more than three mols/mol of intermediate.

Only about two-thirds as much alcohol would be added, on the other hand, when the objective is to replace approximately half of the ester groups of the intermediate.

As indicated in Sabahi, the use of a transesterification process in preparing the lubricants is a particularly desirable method of producing lubricants having higher viscosities, since one of the factors determining the viscosity is the chain lengths of the alkyl groups. However, when an alcohol employed in the process contains higher alkyl groups, e.g., alkyls of 6–30 carbons, it is important to avoid replacing too many of the lower alkyl groups. Whether the lubricants are prepared directly by a Michael reaction or by the transesterification of a Michael product, at least 10%, preferably at least 20%, and more preferably at least 50% of the alkyl groups must contain only 1–4 carbons if the lubricants are to have the desired miscibility with fluorohydrocarbon refrigerants.

Use of a transesterification reaction after completion of the Michael reaction permits a wide variety of products to be prepared from any particular product of the Michael reaction. The transesterification is suitably conducted in the presence or absence of a basic catalyst at an elevated temperature which provides for reflux and removal of a lower alcohol by-product from the reaction mixture without permitting undue loss of the higher alcohol reactant(s) from the reaction vessel, e.g, a temperature of about 50°–180° C.

The products resulting from the Michael reaction or from conversion of the Michael reaction products to transesterified derivatives are typically washed with water to remove any unreacted materials and catalyst prior to being used in their intended application; and, if desired, they may then be further purified by subjecting them to fractional distillation.

Refrigeration compositions of the invention typically comprise 0.001–1, preferably 0.1–1 part of the novel lubricant per part by weight of the refrigerant, and, if desired, they may also contain additives of the type conventionally used in refrigeration lubricants. In addition to epoxy and other dehydrating agents sometimes employed to prevent corrosion of refrigeration equipment by any water in the refrigeration compositions, such additives include, e.g., oxidation resistance and thermal stability improvers, corrosion inhibitors, metal deactivators, lubricity additives, viscosity index improvers, pour and/or floc point depressants, detergents, dispersants, antifoaming agents, anti-wear agents, and extreme pressure resistance additives, such as those exemplified in U.S. Pat. No. 5,021,179 (Zehler et al.), the teachings of which are incorporated herein by reference. As in Zehler et al., these additives, when employed, are generally utilized in small amounts totaling not more than 8%, preferably not more than 5%, of the weight of the lubricant formulation.

The refrigeration compositions are generally formed prior to use. However, when desired, they may also be formed in situ during operation of the refrigeration equipment. Thus, the refrigerant and the lubricant may be charged to the refrigeration equipment separately, either simultaneously or consecutively in either order, instead of being preblended.

Although the invention is advantageous in its provision of refrigeration compositions containing other refrigerants, its greatest value is in its ability to provide refrigeration compositions containing lubricants which are suitable for use with refrigerants and refrigerant mixtures that are environmentally superior to the chlorofluorocarbon refrigerants most commonly used in refrigeration applications—especially fluorohydrocarbon refrigerants such as R-134a. The lubricants of the invention which are apt to be preferred in this regard are the $ROOC-CH_2CH_2-(ROOC-CHCH_2)_m-C(COOR)_2-(CH_2CHCOOR)_n-CH_2CH_2COOR$ oily mixtures in which at least 20%, more preferably at least 50% of the R groups are alkyl groups of 1–4 carbons; up to 80%, e.g., 1–80% of the R groups are alkyl groups of 6–10 carbons, and the sum of m and n in the molecules is an average of 1–10.

The following examples are given to illustrate the invention and are not intended as a limitation thereof.

EXAMPLE 1

Part A

Reaction of dimethyl malonate with methyl acrylate

Charge a suitable reaction vessel with 792 g (6 mols) of dimethyl malonate, 52.8 g (0.4 mol) of potassium carbonate, 12 g (0.035 mol) of tetrabutylammonium hydrogen sulfate, and 1290 g (15 mols) of methyl acrylate. After stirring the reaction mixture at room temperature for ∼18 hours, slowly heat it to ∼50° C. to effect a rapid rise of the temperature of the reaction mixture to reflux. Maintain the reaction mixture at reflux for ∼15 minutes and then cool to room temperature over a period of ∼1 hour. A heavy solid mass forms in the bottom of the reaction vessel during cooling. Dilute this mass with methylene chloride, wash with five 1.5-L portions of water, and subject the product to gas chromatographic (GC) analysis. The analysis shows the product to contain, in area percentages, 60–66% tetramethyl ester of 1,3,3,5-pentanetetracarboxylic acid and 40–34% pentamethyl ester of 1,3,3,5,7-heptanepentacarboxylic acid and other esters of alkanepolyoic acids containing more than two acrylate moieties per molecule.

Parts B and C

Partial transesterifications of methyl ester with hexanol

Part B

Add n-hexanol to the product of Part A in an amount sufficient to replace all of the methyl groups with hexyl groups. Then heat the reactants in the presence of potassium carbonate and a tetraalkylammonium hydrogen sulfate to permit the slow distillation of methanol while monitoring the progress of the transesterification by $^1$H-NMR spectroscopy. Stop the reaction when the —OCH$_3$/—OCH$_2$— ratio shows ∼53% of the methyl groups to have been replaced. The resulting oil has a viscosity of 34.1 mm$^2$.s$^{-1}$ at 40° C., a viscosity of 5.83 mm$^2$.s$^{-1}$ at 100° C., a viscosity index of 113, and miscibility with R-134a at temperatures above 0° C.

Part C

Repeat Part B except for continuing the transesterification until ∼46% of the methyl groups have been replaced. The resulting oil has a viscosity of 39.8 mm$^2$.s$^{-1}$ at 40° C., a viscosity of 6.20 mm$^2$.s$^{-1}$ at 100° C., a viscosity index of 102, and miscibility with R-134a at temperatures of ∼25° C. to 70° C.

COMPARATIVE EXAMPLE A

Complete transesterification of methyl ester with hexanol

Repeat Example 1, Part B, except for continuing the transesterification reaction until all of the methyl groups have been replaced. The product is totally immiscible with R-134a at temperatures of −40° C. to 70° C.—the temperatures generally found in refrigeration equipment.

EXAMPLE 2

Partial transterification of methyl ester with butanol and hexanol

Repeat Example 1, Part B, except for replacing the hexanol with a 1/1 (v/v) mixture of n-butanol and n-hexanol and stopping the reaction when ~20% of the methyl groups have been replaced. The resulting oil has a viscosity of 159.0 $mm^2 \cdot s^{-1}$ at 40° C., a viscosity of 14.60 $mm^2 \cdot s^{-1}$ at 100° C., a viscosity index of 89, and total miscibility with R-134a from −40° C. to 70° C.

EXAMPLE 3

Partial transesterification of methyl ester with butanol and hexanol

Repeat Example 2 except for replacing the mixture of methyl esters with a similar mixture containing at least 95% tetramethyl ester of 1,3,3,5-pentanetetracarboxylic acid and continuing the reaction until 62% of the methoxy groups have been replaced. The resulting oil has a viscosity of 24.1 $mm^2 \cdot s^{-1}$ at 40° C., a viscosity of 4.50 $mm^2 \cdot s^{-1}$ at 100° C., a viscosity index of 97, and total miscibility with R-134a from −40° C. to 70° C.

EXAMPLE 4

Partial transesterification of methyl ester with butanol and hexanol

Repeat Example 3 except for continuing the reaction until 77% of the methyl groups have been replaced. The resulting oil has a viscosity of 24.1 $mm^2 \cdot s^{-1}$ at 40° C., a viscosity of 4.60 $mm^2 \cdot s^{-1}$ at 100° C., a viscosity index of 105, and miscibility with R-134a from 0° C. to 70° C.

EXAMPLE 5

Partial transesterification of methyl ester with butanol and hexanol

Repeat Example 3 except for continuing the reaction until >90% of the methyl groups have been replaced. The resulting oil has a viscosity of 22.0 $mm^2 \cdot s^{-1}$ at 40° C., a viscosity of 4.40 $mm^2 \cdot s^{-1}$ at 100° C., a viscosity index of 112, and miscibility with R-134a at temperatures above 25° C.

EXAMPLE 6

One-pot Michael addition and transesterification

Charge a reaction vessel with 15.8 Kg (120 mols) of dimethyl malonate, 158 g (1.2 mols) of potassium carbonate, and 37 g (0.1 mol) of tetrabutylammonium hydrogen sulfate under nitrogen. Heat the reactor to −70° C., add 25.8 Kg (300 mols) of methyl acrylate over six hours, and then heat the reaction mixture at 70°–80° C. for at least 10 hours to form a product mixture containing a major amount of tetramethyl ester of 1,3,3,5-pentanetetracarboxylic acid, smaller amounts of penta- methyl and higher esters, and a minor amount of trimethyl ester of 1,1,3-propanetricarboxylic acid.

Charge 22 Kg (296 mols) of n-butanol and 30.3 Kg (296 mols) of n-hexanol to the reactor and heat at 110°–120° C. while collecting the volatiles overhead. After removing the stoichiometric amount of methanol, cool the reaction mixture to room temperature, dilute with toluene, wash to neutrality with water, dry by the azeotropic removal of water, and heat treat the crude under reduced pressure.

Distillation under reduced pressure (1 mm Hg) and 200°–250° C. provides an oil which has a viscosity of 17 $mm^2 \cdot s^{-1}$ at 40° C., a viscosity of 3.6 $mm^2 \cdot s^{-1}$ at 100° C., a total acid number (TAN) of 0.025 mgKOH/g, a water content of 64 ppm, and total miscibility with R-134a over a temperature range of −60° C. to 80° C. The bottoms product is an oil having a viscosity of 24.8 $mm^2 \cdot s^{-1}$ at 40° C., a viscosity of 4.7 $mm^2 \cdot s^{-1}$ at 100° C., a total acid number of 0.034 mgKOH/g, a water content of 73 ppm, and total miscibility with R-134a over a temperature range of −60° C. to 80° C.

EXAMPLE 7

Reaction of dimethyl malonate with butyl acrylate

Charge a suitable reaction vessel with 660 g (5 mols) of dimethyl malonate, 35 g (0.25 mol) of potassium carbonate, and 1.75 g (0.005 mol) of tetrabutylammonium hydrogen sulfate. Heat the stirred mixture to 120° C., and add 2048 g (16 mols) of n-butyl acrylate over a period of six hours while monitoring the reaction by GC, which shows the dibutyl dimethyl ester of 1,3,3,5-pentanetetracarboxylic acid to be the major product at the end of this period. Then heat the reaction mixture at 150° C. for three hours to form a product mixture containing the tributyl dimethyl ester of 1,3,3,5,7-heptanepentacarboxylic acid. Cool the resulting reaction mixture to room temperature, add water and toluene, wash repeatedly with water until neutral, remove the water and toluene by azeotropic distillation, and then remove light products at 180°–185° C. and 0.1–0.15 mm Hg to provide a heavy oil having a viscosity of 96 $mm^2 \cdot s^{-1}$ at 40° C., a viscosity of 11.6 $mm^2 \cdot s^{-}$ at 100° C., a viscosity index of 109, and total miscibility with R-134a over a temperature range of −60° C. to 80° C.

What is claimed is:

1. A refrigeration composition comprising a fluorohydrocarbon refrigerant and, as a refrigeration lubricant, at least one oil corresponding to the formula ROOC-CH$_2$CH$_2$-(ROOC-CHCH-$_2$)$_m$-C(COOR)$_2$-(CH$_2$CHCOOR)$_n$-CH$_2$CH$_2$COOR in which the R's represent alkyl groups of 1–30 carbons, at least 10% of which are alkyl groups of 1–4 carbons; each of m and n is zero or a positive integer; and the sum of m and n in the molecules is an average of 0–30.

2. The composition of claim 1 wherein the refrigerant consists of one or more fluorohydrocarbons.

3. The composition of claim 2 wherein the refrigerant is 1,1,1,2-tetrafluoroethane.

4. The composition of claim 1 wherein the refrigerant consists of a mixture of one or more fluorohydrocarbons with one or more other refrigerants.

5. The composition of claim 1 wherein at least 20% of the R groups are alkyl groups of 1–4 carbons and up to 80% are alkyl groups of 6–10 carbons.

6. The composition of claim 5 wherein the refrigerant consists of one or more fluorohydrocarbons.

7. The composition of claim 6 wherein the refrigerant is 1,1,1,2-tetrafluoroethane.

8. The composition of claim 5 wherein the refrigerant consists of a mixture of one or more fluorohydrocarbons with one or more other refrigerants.

9. The composition of claim 5 wherein at least 50% of the R groups are alkyl groups of 1–4 carbons and up to 50% are alkyl groups of 6–10 carbons.

10. The composition of claim 9 wherein the refrigerant consists of one or more fluorohydrocarbons.

11. The composition of claim 10 wherein the refrigerant is 1,1,1,2-tetrafluoroethane.

12. The composition of claim 9 wherein the refrigerant consists of a mixture of one or more fluorohydrocarbons with one or more other refrigerants.

13. The composition of claim 1 wherein the sum of m and n is at least one in at least 25% of the oil molecules.

14. The composition of claim 13 wherein the refrigerant consists of one or more fluorohydrocarbons.

15. The composition of claim 14 wherein the refrigerant is 1,1,1,2-tetrafluoroethane.

16. The composition of claim 13 wherein the refrigerant consists of a mixture of one or more fluorohydrocarbons with one or more other refrigerants.

* * * * *